United States Patent
Radicone (10) Patent No.: US 12,312,267 B2
(45) Date of Patent: May 27, 2025

(54) METHOD, SYSTEM, AND COMPOSITION OF MATTER FOR REDUCING TOXIC MERCURY IN WASTEWATER EFFLUENT

(71) Applicant: i 2 Air Fluid Innovation, Inc., Huntington Station, NY (US)

(72) Inventor: Michael C. Radicone, Huntington Station, NY (US)

(73) Assignee: i 2 Air Fluid Innovation, Inc., Huntington Station, NY (US)

( * ) Notice: Subject to any disclaimer, the term of this patent is extended or adjusted under 35 U.S.C. 154(b) by 482 days.

(21) Appl. No.: 17/945,605

(22) Filed: Sep. 15, 2022

(65) Prior Publication Data

US 2023/0087150 A1    Mar. 23, 2023

Related U.S. Application Data

(60) Provisional application No. 63/245,430, filed on Sep. 17, 2021.

(51) Int. Cl.
*C02F 3/34* (2023.01)
*A61C 17/06* (2006.01)
(Continued)

(52) U.S. Cl.
CPC ............ *C02F 3/341* (2013.01); *A61C 17/065* (2019.05); *C02F 3/10* (2013.01); *C12N 1/20* (2013.01);
(Continued)

(58) Field of Classification Search
CPC .. C02F 3/341; C02F 3/10; C02F 3/348; C02F 2101/20; C02F 2101/30; C02F 2103/006;
(Continued)

(56) References Cited

U.S. PATENT DOCUMENTS

| 4,728,427 A |  | 3/1988 | Revis et al. |
| 6,620,321 B2 | * | 9/2003 | Festa ........................ C02F 3/288 |
|  |  |  | 210/150 |

(Continued)

FOREIGN PATENT DOCUMENTS

| DE | 4227769 A1 | * | 2/1994 | ............... A62D 3/02 |
| TW | 201527227 A | * | 7/2015 |  |
| WO | WO-2012162518 A2 | * | 11/2012 | .............. C02F 3/006 |

OTHER PUBLICATIONS

Machine-generated English translation of DE 4227769, generated on Mar. 4, 2025.*

(Continued)

*Primary Examiner* — Fred Prince
(74) *Attorney, Agent, or Firm* — Stites & Harbison, PLLC; David W. Nagle, Jr.; James R. Hayne (57) ABSTRACT

A method for reducing toxic mercury in wastewater effluent comprises the steps of: identifying a system into which wastewater effluent is introduced, the wastewater effluent including organic compounds and organomercurial compounds; producing a treatment composition comprising a solution including a surfactant, digestive microbes suspended in the solution, and mercury-transformative microbes suspended in the solution; and providing the treatment composition into the system containing the wastewater effluent, such that the digestive microbes degrade the organic compounds in the wastewater effluent, and the mercury-transformative microbes reduce the organomercurial compounds in the wastewater effluent into nontoxic volatile elemental mercury. In certain systems for reducing toxic mercury in wastewater effluent, a biological capture medium is positioned within a vessel and configured to provide a capture point for microbes to adhere to and create biofilms. One such system is a dental evacuation system in (Continued)

which wastewater effluent is introduced into the system via an aspirator.

24 Claims, 3 Drawing Sheets

(51) Int. Cl.
  *C02F 3/10*    (2023.01)
  *C12N 1/20*    (2006.01)
  *C02F 101/20*   (2006.01)
  *C02F 101/30*   (2006.01)
  *C02F 103/00*   (2006.01)
  *C12R 1/07*    (2006.01)

(52) U.S. Cl.
  CPC .............. *A61C 17/06* (2019.05); *C02F 3/348* (2013.01); *C02F 2101/20* (2013.01); *C02F 2101/30* (2013.01); *C02F 2103/006* (2013.01); *C02F 2303/26* (2013.01); *C02F 2305/04* (2013.01); *C12R 2001/07* (2021.05); *C12Y 116/01001* (2013.01); *C12Y 499/01002* (2013.01)

(58) Field of Classification Search
  CPC ............. C02F 2303/26; C02F 2305/04; A61C 17/065; A61C 17/06; C12N 1/20; C12R 2001/07; C12Y 116/01001; C12Y 499/01002
  USPC .......... 210/615, 150, 151, 620, 914
  See application file for complete search history.

(56) References Cited

U.S. PATENT DOCUMENTS

| | | | |
|---|---|---|---|
| 8,846,376 B2 | 9/2014 | Seeger Pfeiffer et al. | |
| 2001/0047956 A1* | 12/2001 | Albiston | C02F 9/00 210/138 |
| 2006/0065594 A1* | 3/2006 | Armstrong | C02F 1/5236 210/663 |
| 2010/0133195 A1 | 6/2010 | Gane et al. | |
| 2012/0171128 A1 | 7/2012 | Ramirez | |
| 2020/0002240 A1 | 1/2020 | Conley et al. | |

OTHER PUBLICATIONS

Machine-generated English translation of TW 201527227, generated on Mar. 4, 2025.*
Korean Intellectual Property Office, International Search Report and Written Opinion issued in corresponding Application No. PCT/US2022/043640, mailed Jan. 10, 2023.
Solmetex, PowerScrub Vacuum Line Cleaner, https://solmetex.com/powerscrub/ (downloaded Jan. 20, 2023).

* cited by examiner

METHOD, SYSTEM, AND COMPOSITION OF MATTER FOR REDUCING TOXIC MERCURY IN WASTEWATER EFFLUENT

CROSS-REFERENCE TO RELATED APPLICATIONS

This application claims priority from U.S. Provisional Application Ser. No. 63/245,430, filed Sep. 17, 2021, the entire disclosure of which is incorporated herein by this reference.

BACKGROUND OF THE INVENTION

Mercury ions exists in three forms: elemental, inorganic, and organic. Most mercury compounds are highly cytotoxic to all life forms, including bacteria, fish, and humans. Mercury compounds are presented to the environment through wastewater effluent. For example, mercury compounds may be present in wastewater effluent from industrial and mining operations. For another example, wastewater effluent from dental procedures from orally evacuated fluids can include mercury compounds, because silver amalgam fillings ordinarily contain mercury. Once in the environment, mercury compounds can move up the food chain from plankton to fish to humans.

Digestive microbes that produce enzymes are capable of degrading proteins, fats, etc., and have been used in dental evacuation systems to reduce organic foul and to maintain their functionality. Such digestive microbes produce a myriad of enzymes that reduce foul formation. Unfortunately, and as noted above, toxic mercury compounds are often present within the orally evacuated wastewater effluent. They are highly cytotoxic to many of the digestive microbes used for dental evacuation system cleaning. Toxic mercury ions can reduce or nullify the function of the digestive microbes through cellular damage, death, or reducing microbial numbers. Additionally, it is known that mercury ions have a degrading effect on the protease enzyme, one of the key enzymes in foul degradation.

Although many microbes are damaged by toxic mercury ions, certain bacteria, fungi and mold species have developed the ability to transform toxic inorganic and organic mercury into inert elemental mercury for self-protection and as an energy source. Quantitatively, the total mercury content does not change, but in an elemental form, the mercury ions are less toxic. The microbes effectuate this transformation through the release of transformative enzymes by specified genes. The genes responsible present merA and merB, which are the enzymes mercuric reductase and organomercurial lyase. The lyase reduces the highly toxic organomercurial compounds into almost nontoxic volatile elemental mercury, while the mercuric reductase is responsible for the transfer of electrons. This transformative ability has been explored for decades as a potential means of environmental mercury remediation, but its application in dental evacuation systems (which are a significant mercury source) and to other wastewater effluents has never been fully investigated. At the same time, however, the Environmental Protection Agency (EPA) and other agencies worldwide have demanded a reduction in mercury expression to the environment via wastewater effluent from dental procedures.

SUMMARY OF THE INVENTION

The present invention is directed to a method, system, and composition of matter for reducing toxic mercury in wastewater effluent.

According to some exemplary implementations of the present invention, a method for reducing toxic mercury in wastewater effluent begins with a step of producing a treatment composition comprising a solution including a surfactant, digestive microbes suspended in the solution, and mercury-transformative microbes suspended in the solution. When producing the treatment composition, the mercury-transformative microbes are introduced to low levels of methyl chloride within a growth medium such that merA and merB genes are expressed in reproduced microbes. Next, the treatment composition is provided into a system containing the wastewater effluent, such that the digestive microbes degrade organic compounds in the wastewater effluent, and the mercury-transformative microbes reduce organomercurial compounds in the wastewater effluent into nontoxic volatile elemental mercury.

According to some exemplary implementations, the method further includes a step of generating air bubbles in the treatment composition while the treatment composition is introduced into the system.

In some exemplary embodiments of the present invention, a system includes an inlet through which the wastewater effluent is introduced into the system, an outlet through which the wastewater effluent leaves the system, a vessel positioned between the inlet and the outlet, and a biological capture medium positioned within the vessel. The biological capture medium is configured to provide a capture point for microbes to adhere to and create biofilms.

In some exemplary embodiments, the vessel includes an interior surface, and the biological capture medium is attached to the interior surface of the vessel.

In some exemplary embodiments, the biological capture medium is positioned within the vessel such that all of the wastewater effluent passes through the biological capture medium.

In some exemplary embodiments, the biological capture medium is suspended in the vessel.

In some exemplary embodiments, the biological capture medium floats within the wastewater effluent inside the vessel.

In some exemplary embodiments, the vessel contains a treatment composition comprising a solution including a surfactant, digestive microbes suspended in the solution, and mercury-transformative microbes suspended in the solution.

In the case of some such embodiments, the treatment composition forms a biofilm of the digestive microbes and the mercury-transformative microbes on the interior surface of the vessel.

In the case of some such embodiments, the treatment composition is introduced into the system via the inlet. According to some particular embodiments, when the treatment composition is introduced into the system, the inlet is configured to introduce air into the treatment composition and generate air bubbles in the treatment composition.

In some exemplary embodiments, the digestive microbes include *bacillus* spore-forming and non-pathogenic microbes, the mercury-transformative microbes have enhanced merA and merB enzyme gene expression, and the surfactant is an adhesion surfactant.

In some exemplary embodiments, there are approximately $4 \times 10^7$ digestive microbes and mercury-transformative microbes per mL of the solution.

In some exemplary embodiments, the mercury-transformative microbes are capable of transforming 80,000 ppb of mercuric chloride ions (Hg+2) into inert (Hg0) in 24 hours.

In some exemplary embodiments, when the treatment composition is agitated, the surfactant maintains a bubble emulsion.

In some exemplary embodiments of the present invention, the system is a dental evacuation system, and the inlet is an aspirator which is used to introduce a treatment composition into the system. Some exemplary dental evacuation systems further include a biological capture medium positioned within the vessel, the biological capture medium configured to provide a capture point for digestive microbes and mercury-transformative microbes to adhere to and create biofilms. In such systems, the digestive microbes reduce organic foul within the wastewater effluent, and the mercury-transformative microbes transform mercuric chloride ions (Hg+2) within the wastewater effluent into inert (Hg0).

In some exemplary dental evacuation systems, the aspirator is configured to introduce a treatment composition into the dental evacuation system along with air, such that air bubbles are generated in the treatment composition. The treatment composition includes a solution including a surfactant, digestive microbes suspended in the solution, and mercury-transformative microbes suspended in the solution.

According to some exemplary implementations of the present invention, a method for reducing toxic mercury in wastewater effluent begins with a step of identifying a system into which wastewater effluent is introduced, the wastewater effluent including organic compounds and organomercurial compounds. A treatment composition is produced, with the treatment composition comprising a solution including a surfactant, digestive microbes suspended in the solution, and mercury-transformative microbes suspended in the solution. The treatment composition is provided into the system containing the wastewater effluent such that the digestive microbes degrade the organic compounds in the wastewater effluent, and the mercury-transformative microbes reduce the organomercurial compounds in the wastewater effluent into nontoxic volatile elemental mercury.

According to some exemplary implementations, the step of producing the treatment composition includes introducing the mercury-transformative microbes to low levels of methyl chloride within a growth medium such that merA and merB genes are expressed in reproduced microbes.

According to some exemplary implementations, the method further includes a step of generating air bubbles in the treatment composition while the treatment composition is introduced into the system.

In some exemplary formulations of the present invention, a composition of matter for reducing toxic mercury in wastewater effluent includes digestive microbes that reduce organic foul within the wastewater effluent, mercury-transformative microbes that produce mercuric reductase and organomercurial lyase, and a solution including a surfactant. In such embodiments, the mercury-transformative microbes of the composition have been introduced to low levels of methyl chloride within a growth medium such that merA and merB genes are expressed in reproduced microbes. Furthermore, the digestive microbes and the mercury-transformative microbes are suspended in the solution.

In some exemplary formulations, the mercury-transformative microbes have enhanced merA and merB enzyme gene expression.

In some exemplary formulations, the mercury-transformative microbes are capable of transforming 80,000 ppb of mercuric chloride ions (Hg+2) into inert (Hg0) in 24 hours.

In some exemplary formulations, the composition is agitated to generate air bubbles and the surfactant maintains a bubble emulsion.

DETAILED DESCRIPTION OF THE INVENTION

The present invention is a method, system, and composition of matter for reducing toxic mercury in wastewater effluent, which, in some embodiments, have particular applicability to dental evacuation systems.

In one exemplary embodiment of the present invention, a composition of matter includes digestive microbes which are combined with (i) mercury-transformative microbes and (ii) a solution of water and a surfactant providing adhesion, wetting, and/or blending benefits, resulting in a treatment composition for wastewater effluent, as further discussed below.

In accordance with some exemplary embodiments of the present invention, the digestive microbes include *bacillus* spore-forming and non-pathogenic microbes which produce enzymes, including protease and amalase. However, other microbes that produce a myriad of enzymes to reduce organic foul are also well known and can be used without departing from the spirit and scope of the present invention.

Unfortunately, when toxic mercury compounds are present along with amalgam particles, the mercury compounds are highly cytotoxic to many of the digestive microbes. Toxic mercury ions can reduce or nullify the digestive microbes capabilities through cellular damage, death, or reducing microbial numbers. Additionally, it is known that mercury ions have a degrading effect on the protease enzyme, one of the key enzymes in foul degradation. Advantageously, the inclusion of mercuric transformative digestive microbes in the composition of the present invention provides not only self-protection, but also provides extra cellular protection to non-transformative microbes and reduces free floating toxic mercury ions. According to some exemplary embodiments of the present invention, the mercury-transformative microbes have enhanced merA and merB enzyme gene expression, and therefore produce mercuric reductase and organomercurial lyase. In operation, the mercury-transformative microbes included in the treatment composition are capable of transforming 80,000 ppb of mercuric chloride ions (Hg+2) into inert (Hg0) in 24 hours. Furthermore, in some exemplary formulations, there are approximately $4 \times 10^7$ microbes (e.g., the digestive microbes and the mercury-transformative microbes) per mL in the treatment composition.

With respect to the production and harvesting of such mercury-transformative microbes, according to some exemplary implementations of the present invention, the mercury-transformative microbes are introduced to extremely low levels of methyl chloride within a growth medium. This induces merA and merB gene expression in the reproduced microbes during multiplication, but as the microbes undergo their life cycle within the harvesting tank, they convert the methyl mercury into inert mercury, thus eliminating toxic ions in the final microbial blend.

Figure 1:
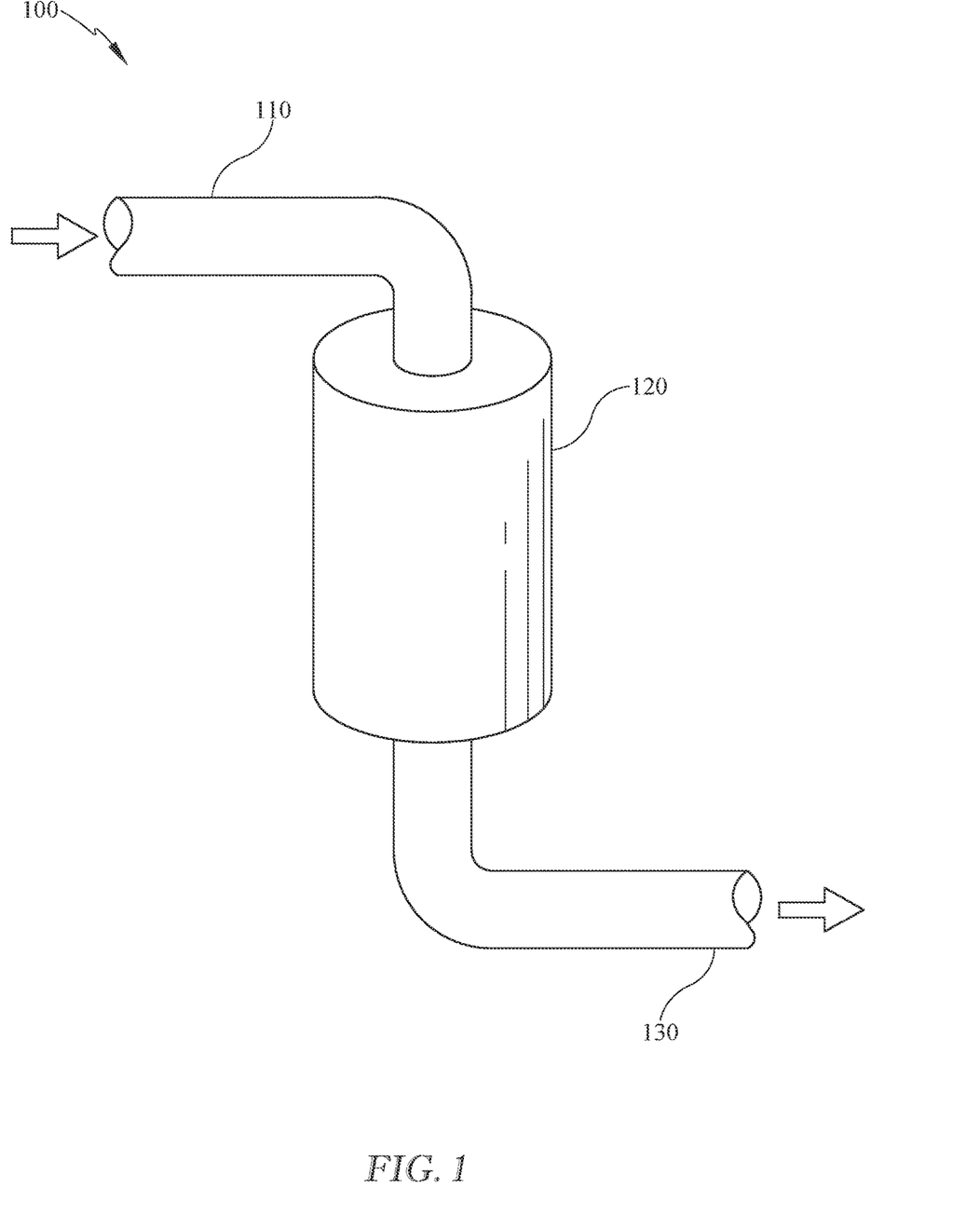
FIG. 1 is a perspective view of an exemplary system for reducing toxic mercury in wastewater effluent made in accordance with the present invention.

Referring now to FIG. 1, in one simplified exemplary system 100 made in accordance with the present invention, wastewater effluent is introduced into the system 100 via an inlet 110 before passing through an interaction vessel 120 and leaving the system 100 via an outlet 130.

As described above, the exemplary treatment composition includes both digestive microbes and mercury-transformative microbes in a solution of water and a surfactant. According to some exemplary embodiments of the present invention, the surfactant is one of the following: hexadecyl trimethyl ammonium bromide (HTAB); sodium dodecylbenzene sulphonate (SDBS); or Tergitol®. (Tergitol® is a registered trademark of Union Carbide Corporation of Seadrift, Texas) However, other cationic, anionic, and/or nonionic surfactants can be used without departing from the spirit and scope of the present invention. Regardless of the particular surfactant used, the surfactant facilitates uniform distribution of the treatment composition within the system and also facilitates placement of the microbes directly on foulants.

According to some exemplary implementations, the treatment composition of microbes and surfactant solution is agitated to generate nano or micro air bubbles within the composition. This creates a bubble emulsion which provides oxygen aeration for the aerobic microbe's preservation and growth. The bubble surfaces also provide an increased surface area onto which the microbes may attach. Advantageously, inclusion of the surfactant also maintains a bubble emulsion which resists gas off.

Furthermore, the surfactant also facilitates placement of the microbes on wall surfaces. This allow for the microbes to more readily stay in place against dynamic water or air flow through the system therefore reducing downstream movement of the microbes, which allows for multiplication and growth at the sites most requiring treatment. In other words, the surfactant improves cellular attachment, anchoring, and colonization of the microbes providing enhanced enzyme formation and expression.

Figure 2:
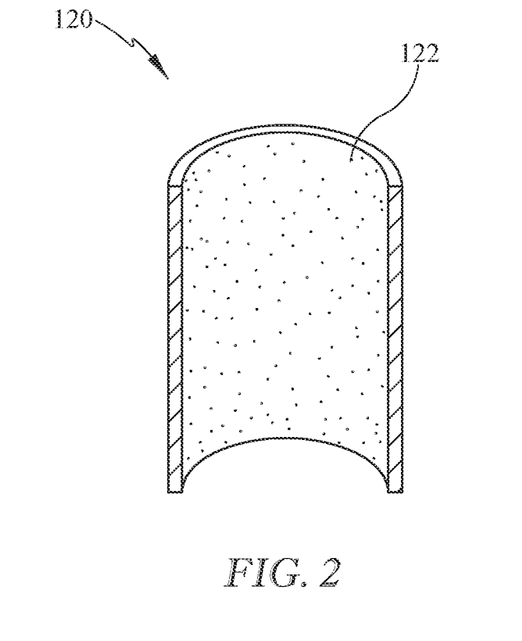
FIG. 2 is a cross-sectional schematic view of the interaction vessel of the system of FIG. 1, illustrating a biofilm that is formed on the interior surface of the interaction vessel.

Specifically, and referring now to FIG. 2, according to some embodiments, the adhesion surfactants allow the microbes (e.g., the digestive microbes and the mercury-transformative microbes) to adhere to the interior surface 122 of the interaction vessel 120. These attachment sites allow for the colonization and multiplication of enzyme-producing microbes. Eventually, layers of biofilm, in which there are immobilized microbes, are formed on the interior surface 122. The immobilized microbes continue to produce enzymes which are presented into the wastewater effluent passing through the interaction vessel 120. Accordingly, not only do the expressed enzymes provide digestion and transformation within the interaction vessel 120, but the continually expressed enzymes provide downstream digestion or transformation as well. This allows for a residual expression of enzymes of wastewater effluent passing through the outlet 130, as well as through any additional downstream components. Although a lack of organic compounds and mercuric ions will eventually cause the biofilm microbes to die off, a periodic re-introduction of treatment composition will either reinvigorate the biofilm or create new biofilms. Furthermore, it is contemplated that even dead transformative microbes can release mercuric transformative enzymes.

Although haphazard biofilms can provide residual enzyme presentation, in order to target enzyme release into a particular location of the system, i.e., the interaction vessel, according to some exemplary systems of the present invention, a biological capture medium is positioned within the interaction vessel to promote targeted biofilm growth.

Figure 3:
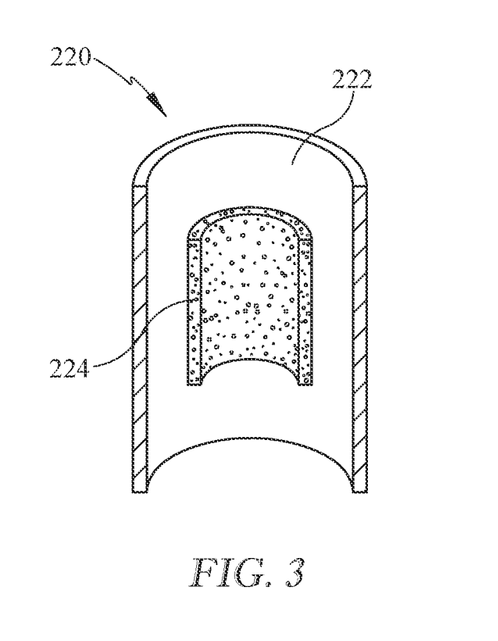
FIG. 3 is a cross-sectional schematic view of another exemplary interaction vessel, illustrating a biological capture medium that is attached to the interior surface of the interaction vessel.

Referring now to FIG. 3, in one exemplary embodiment, a biological capture medium 224 is adhered to the interior surface 222 of the interaction vessel 220. The biological capture medium 224 can be made of a variety of materials known in the art, including materials that are made from or contain mercury compounds and which allow fluid and particles to flow into and through the biological capture medium 224. The exemplary biological capture medium 224 shown in FIG. 3 is called a mercuric sponge. As the mercuric sponge 224 is exposed to the microbes, adhesion surfactants, aerated fluids, and mercuric ions, the mercuric sponge 224 provide a capture point for the microbes (e.g., the digestive microbes and the mercury-transformative microbes) to adhere to and create biofilms. The mercuric sponge 224 thereby provides the means for microbial growth, multiplication, biofilm formation, and enzyme release within the interaction vessel 220.

To help stimulate microbial colonization, according to some exemplary embodiments, dry forms of the digestive microbes and/or the mercury transformative microbes are adhered to the material of the mercuric sponge 224, along with a growth-enhancing nutrient agar. Additional sulfur-reducing microbes can also be included, as it is contemplated that these sulfur-reducing microbes enhance mercury capture or transformation. The nutrients, which may include sulfur as a nutrient for sulfur reducing microbes as well as mercury capture, along with oxygen/air bubbles, provide for a rapid multiplication and growth phase to induce enzyme generation and release. When immobilized within a biofilm or agar gel formed on the mercuric sponge 224, the microbes continue to release enzymes and capture insoluble inert mercuric ions. Additionally, even when microbes have died (e.g., due to disinfection or lack of nutrients) when they are presented to fluids containing toxic soluble mercury ions, there is a rapid release of the mercuric reductase enzyme from the cytoplasm. It is contemplated that this provides an acute transformation of mercuric ions, which can be of particular advantage for use in septic systems to reduce discharged fecal and urine matter containing toxic mercuric ions.

While the exemplary mercuric sponge 224 is shown as a rectangular patch that covers only a portion of the interior surface 222 of the interaction vessel 220, the size, shape, and placement of the mercuric sponge 224 is not limited, and, in some embodiments, the mercuric sponge can cover substantially all of the interior surface of an interaction vessel 220.

Figure 4:
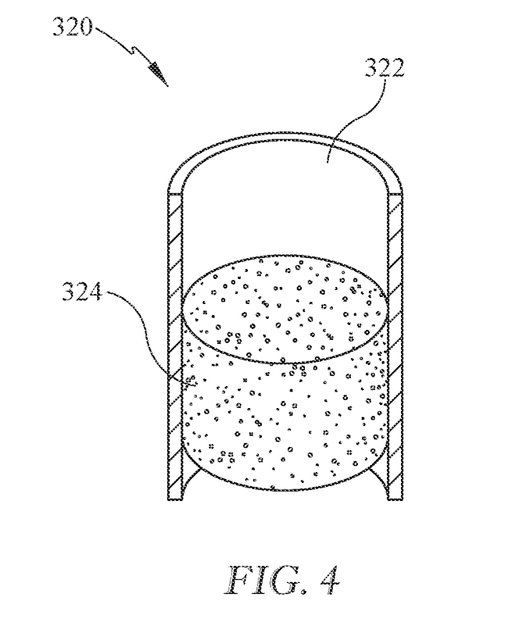
FIG. 4 is a cross-sectional schematic of another exemplary interaction vessel, illustrating a biological capture medium that fills a cross section of the interaction vessel.

Furthermore, and referring now to FIG. 4, in some other exemplary embodiments of the present invention, the biological capture medium 324 is positioned within interaction vessel 320 so as to substantially fill a cross section of the interaction vessel 320, such that all of the wastewater effluent passes through the biological capture medium 324.

For example, the biological capture medium 324 may be part of a filter that is placed in the flow stream through which a fluid containing particles and soluble mercuric ions flow. The exemplary biological capture medium 324 shown in FIG. 4 is called an instream mercuric sponge, and it remains within the flow space, such that, upon the reintroduction of new microbes, adhesion surfactants, aerated fluids, and mercuric ions, the microbes release mercuric and digestive enzymes for downstream presentation into devices, tubing, drains, or the environment. As such, the instream mercuric sponge 324 provides for the continued transformation of mercuric ions within the flow stream and fluidic enzyme presentation post the instream mercuric sponge 324.

Figure 5:
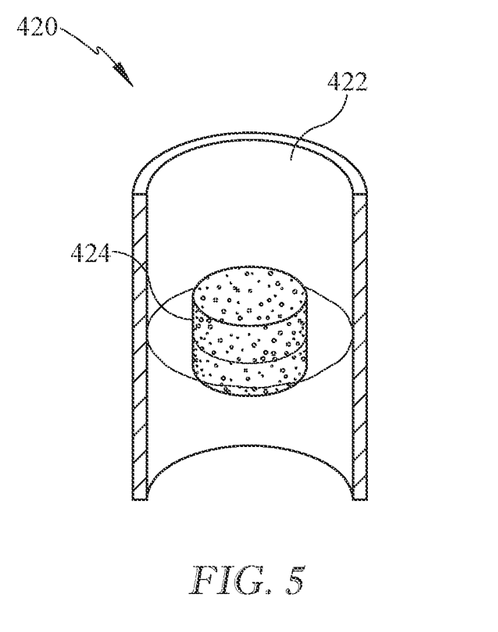
FIG. 5 is a cross-sectional schematic of another exemplary interaction vessel, illustrating a biological capture medium that is suspended in the interaction vessel.

Referring now to FIG. 5, in some other exemplary embodiments of the present invention, the biological capture medium 424 is suspended in the interaction vessel 420. In this exemplary embodiment, the biological capture medium 424 floats within the wastewater effluent inside of the interaction vessel 420 completely detached from the interior surface 422 of the interaction vessel 420. However, in implementations where fluid constantly fills the interaction vessel 420 or flows at a rate which would prevent the biological capture medium 424 from maintaining its position within the interaction vessel 420, a similar biological capture medium may be hung or otherwise loosely connected to the interaction vessel 420. Advantageously, as the biological capture medium 424 is not connected to the interior surface 422, it provides greater surface area per volume for increased exchanges with the wastewater effluent.

Figure 6:
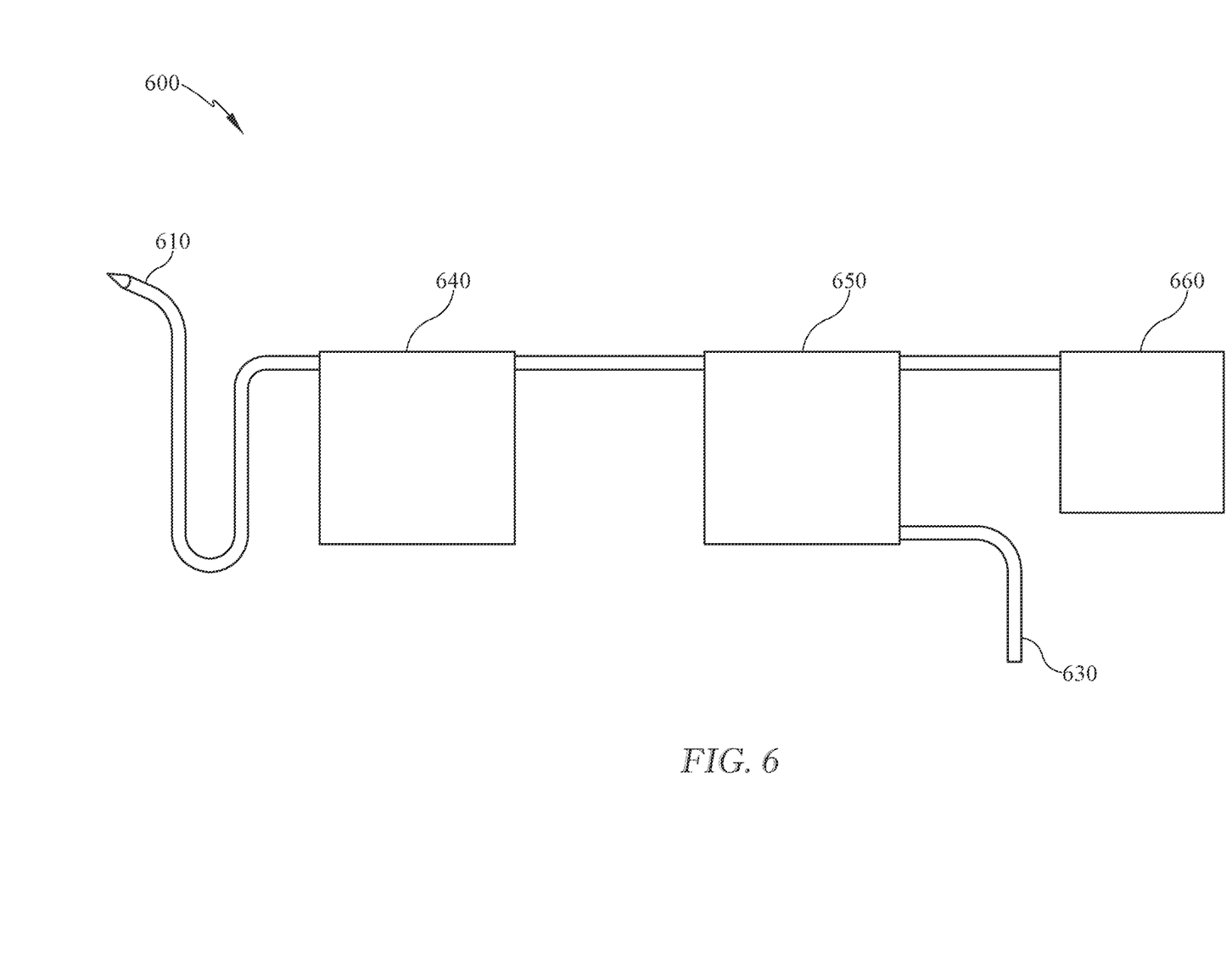
FIG. 6 is a schematic view of an exemplary dental evacuation system for reducing toxic mercury in wastewater effluent made in accordance with the present invention.

As mentioned above, the method, system, and composition of matter of the present invention are believed to have particular applicability to dental evacuation systems. Referring now to FIG. 6, one such exemplary dental evacuation system 600 includes an aspirator 610, debris collector 640, separator 650, and a vacuum source 660. The aspirator 610 operates as an inlet to the system and is used to extract the liquid and dental debris from a dental patient's mouth during a dental procedure. The liquid and debris, collectively corresponding to the wastewater effluent discussed above, travels from the aspirator 610 to the debris collector 640 via a flexible hose or the like. The debris collector 640 then removes the solid debris, while the remaining liquid and vacuum air passes to the separator 650. The vacuum which enters the separator 650 is a "wet vacuum," since it includes both air and liquid. In the separator 650, the liquid is separated from the wet vacuum and collected in the separator 650, and a "dry vacuum" exits from the separator 650 and returns to the vacuum source 660. Liquid collected in the separator 650 then exits the system 600 via an outlet 630 in the separator 650.

In the context of the exemplary dental evacuation system 600, in operation, the treatment composition is introduced into the system 600 via the aspirator 610. Specifically, the aspirator 610 is used to draw the solution into the dental evacuation system while simultaneously drawing air into the aspirator 610 as well, thereby generating nano or micro air bubbles within the treatment composition. Once again, this agitation and bubble formation provides oxygen aeration for the aerobic microbe's preservation and growth.

This bubble emulsion travels to the other components of the dental evacuation system 600. Once introduced, the surfactant of the treatment composition allows the digestive microbes and the mercury-transformative microbes to adhere to internal surfaces of the system, providing for the colonization and multiplication of enzyme-producing mercury-transformative microbes. The surfactants further allow for the microbes to stay in place against dynamic water or air flow. Within the dental evacuation system 600, the mercury-transformative microbes produce enzymes which are presented into the wastewater effluent carrying mercury compounds. The continually expressed enzymes provide downstream digestion and transformation of toxic inorganic and organic mercury into inert elemental mercury.

The dental evacuation system 600 presents an environment where dynamic flow can hinder the effectiveness of digestive microbes by minimizing enzyme exposure or limiting their residence time on surfaces. These conditions would affect anticipated mercury transformation as well. It is therefore paramount to ensure the microbes have time for attachment, replication, enzyme presentation, and perseverance (for residual effect). To achieve these goals, one or more of the interaction vessels 120, 220, 320, 420 described above with respect to FIGS. 1-5 are incorporated into the dental evacuation system 600 in order to enhance and prolong the expression of both digestive and transformative enzymes. It is contemplated that any number of components of the dental evacuation system can operate as one of the interaction vessels 120, 220, 320, 420. Specifically, the debris collector 640, the separator 650, some subcomponent thereof, can operate as an interaction vessel of the present invention. Alternatively, an additional interaction vessel can be included elsewhere in the system. Of course, one skilled in the art will readily recognize what portion(s) of an existing dental evacuation system can be modified to operate as the interaction vessel and/or where an additional component can be added.

Although details are provided for a dental evacuation system 600, in other applications, the treatment composition can be similarly drawn into the conduits or vessels of other systems in which wastewater effluent carrying mercury compounds flows or is present. In still other applications, the treatment solution can be added to a static fluid volume containing mercury compounds and agitated to incorporate air. In any event, as a first step of reducing toxic mercury in wastewater effluent, a system is identified which has wastewater effluent that includes organic compounds and organomercurial compounds.

One of ordinary skill in the art will recognize that additional embodiments and implementations are also possible without departing from the teachings of the present invention or the scope of the claims which follow. This description, and particularly the specific details of the exemplary embodiments and implementations disclosed, is given primarily for clarity of understanding, and no unnecessary limitations are to be understood therefrom, for modifications will become obvious to those skilled in the art upon reading this disclosure and may be made without departing from the spirit or scope of the claimed invention.

What is claimed is:

1. A method for reducing toxic mercury in wastewater effluent, comprising the steps of:
producing a treatment composition comprising a solution including a surfactant, digestive microbes suspended in the solution, and mercury-transformative microbes suspended in the solution; and
providing the treatment composition into a system containing the wastewater effluent such that the digestive microbes degrade organic compounds in the wastewater effluent, and the mercury-transformative microbes reduce organomercurial compounds in the wastewater effluent into nontoxic volatile elemental mercury;
wherein the step of producing the treatment composition includes introducing the mercury-transformative microbes to low levels of methyl chloride within a growth medium such that merA and merB genes are expressed in reproduced microbes.

2. The method as recited in claim 1, and further comprising the step of:
generating air bubbles in the treatment composition while the treatment composition is introduced into the system.

3. A system for reducing toxic mercury in wastewater effluent, the system comprising:
an inlet through which the wastewater effluent is introduced into the system;
an outlet through which the wastewater effluent leaves the system;
a vessel positioned between the inlet and the outlet, wherein the vessel contains a treatment composition comprising a solution including a surfactant, digestive microbes suspended in the solution, and mercury-transformative microbes suspended in the solution; and
a biological capture medium positioned within the vessel, the biological capture medium configured to provide a capture point for microbes to adhere to and create biofilms.

4. The system of claim 3, wherein the vessel includes an interior surface, and the biological capture medium is attached to the interior surface of the vessel.

5. The system of claim 3, wherein the biological capture medium is positioned within the vessel such that all of the wastewater effluent passes through the biological capture medium.

6. The system of claim 3, wherein the biological capture medium is suspended in the vessel.

7. The system of claim 6, wherein the biological capture medium floats within the wastewater effluent inside the vessel.

8. The system of claim 3, wherein the vessel includes an interior surface, and the treatment composition forms a biofilm of the digestive microbes and the mercury-transformative microbes on the interior surface of the vessel.

9. The system of claim 3, wherein the treatment composition is introduced into the system via the inlet.

10. The system of claim 9, wherein when the treatment composition is introduced into the system, the inlet is configured to introduce air into the treatment composition and generate air bubbles in the treatment composition.

11. The system of claim 3, wherein the digestive microbes include *bacillus* spore-forming and non-pathogenic microbes, the mercury-transformative microbes have enhanced merA and merB enzyme gene expression, and the surfactant is an adhesion surfactant.

12. The system of claim 3, wherein there are approximately $4 \times 10^7$ digestive microbes and mercury-transformative microbes per mL of the solution.

13. The system of claim 3, wherein the mercury-transformative microbes are capable of transforming 80,000 ppb of mercuric chloride ions (Hg+2) into inert (Hg0) in 24 hours.

14. The system of claim 3, wherein, when the treatment composition is agitated, the surfactant maintains a bubble emulsion.

15. The system of claim 3, wherein the system is a dental evacuation system and the inlet is an aspirator which is used to introduce a treatment composition into the system, the treatment composition comprising a solution including a surfactant, digestive microbes suspended in the solution, and mercury-transformative microbes suspended in the solution.

16. A dental evacuation system, comprising:

an aspirator through which wastewater effluent is introduced into the dental evacuation system;

an outlet through which the wastewater effluent leaves the dental evacuation system;

a vessel positioned between the aspirator and the outlet; and a biological capture medium positioned within the vessel, the biological capture medium configured to provide a capture point for digestive microbes and mercury-transformative microbes to adhere to and create biofilms;

wherein the digestive microbes reduce organic foul within the wastewater effluent, and the mercury-transformative microbes transform mercuric chloride ions ($Hg+2$) within the wastewater effluent into inert ($Hg0$).

17. The dental evacuation system of claim 16, wherein the aspirator is configured to introduce a treatment composition into the dental evacuation system along with air, such that air bubbles are generated in the treatment composition;

wherein, the treatment composition includes a solution including a surfactant, digestive microbes suspended in the solution, and mercury-transformative microbes suspended in the solution.

18. A method for reducing toxic mercury in wastewater effluent, comprising the steps of:

identifying a system into which wastewater effluent is introduced, the wastewater effluent including organic compounds and organomercurial compounds;

producing a treatment composition comprising a solution including a surfactant, digestive microbes suspended in the solution, and mercury-transformative microbes suspended in the solution; and providing the treatment composition into the system containing the wastewater effluent, such that the digestive microbes degrade the organic compounds in the wastewater effluent, and the mercury-transformative microbes reduce the organomercurial compounds in the wastewater effluent into nontoxic volatile elemental mercury.

19. The method as recited in claim 18, wherein the step of producing the treatment composition includes introducing the mercury-transformative microbes to low levels of methyl chloride within a growth medium such that merA and merB genes are expressed in reproduced microbes.

20. The method as recited in claim 18, and further comprising the step of:

generating air bubbles in the treatment composition while the treatment composition is introduced into the system.

21. A composition of matter for reducing toxic mercury in wastewater effluent, the composition comprising:

digestive microbes that reduce organic foul within the wastewater effluent;

mercury-transformative microbes that produce mercuric reductase and organomercurial lyase, the mercury-transformative microbes having been introduced to low levels of methyl chloride within a growth medium such that merA and merB genes are expressed in reproduced microbes; and a solution including a surfactant;

wherein the digestive microbes and the mercury-transformative microbes are suspended in the solution.

22. The composition of claim 21, wherein the mercury-transformative microbes have enhanced merA and merB enzyme gene expression.

23. The composition of claim 21, wherein the mercury-transformative microbes are capable of transforming 80,000 ppb of mercuric chloride ions (Hg+2) into inert (Hg0) in 24 hours.

24. The composition of claim 21, wherein the composition is agitated to generate air bubbles and the surfactant maintains a bubble emulsion.

* * * * *